United States Patent [19]

Bach

[11] Patent Number: 4,867,559

[45] Date of Patent: Sep. 19, 1989

[54] LIQUID/LIQUID FIBER-OPTIC FLUORESCENCE DETECTOR AND ABSORBANCE ANALYZER

[75] Inventor: David T. Bach, Westborough, Mass.

[73] Assignee: Amoco Corporation, Chicago, Ill.

[21] Appl. No.: 141,159

[22] Filed: Jan. 6, 1988

[51] Int. Cl.⁴ ..................... G01N 21/59; G01N 21/64
[52] U.S. Cl. ................................. 356/73; 250/458.1; 356/318; 356/417; 356/440
[58] Field of Search ................. 356/73, 317, 318, 417, 356/246, 36, 440; 250/458.1, 459.1, 461.1, 461.2

[56] References Cited

U.S. PATENT DOCUMENTS

| | | | |
|---|---|---|---|
| 2,827,825 | 3/1958 | White | 356/301 |
| 3,918,812 | 11/1975 | Holm | 356/73 |
| 3,920,334 | 11/1975 | Steichen et al. | 356/73 |
| 4,371,897 | 2/1983 | Kramer | 250/227 |
| 4,488,814 | 12/1984 | Johnson | 356/417 |
| 4,730,922 | 3/1988 | Bach et al. | 356/73 |

OTHER PUBLICATIONS

Morz & Lechene, "Fluorescence Analysis of Picoliter Samples", Anal. Biochem. 102, 90–96, (1980).
Lovell, "Integrating Sphere Performance", Labsphere, North Sutton, New Hampshire, 1981.
Brady & Frantz, "A Microanalytical Technique for Determination of Aluminum in Aqueous Solutions", Am. Minerol, 65, 1249–1251, 1980.
Kelley & Christian, "Fluorometer for Flow Injection . . .", Anal. Chem., 1981, 53, 2110–2114.
Kelley & Christian, "Capillary Flow Injection Analysis . . . ", Anal. Chem., 1982, 54, 1444–1445.
Papayan et al., "Contact Operating Microfluorometer", Sov. J. Opt. Technol. 51 (2), Feb. 1984, 97–99.
Steindel & Schoudt, "An Assessment of Random Access Fluid Technology", Journal of Clinical Lab. Automation, vol. 3, No. 5:319–326, 1983.
Chaney, "Applications of Fluid Mechanics in Continuous Flow . . . ", Technocon Symposium, Oct. 3, 1967, New York, New York.
Sernetz, "Microcapillary Fluoremetry . . . ", Fluorescence Technology Cell Biology, 1973, 41–49.

Primary Examiner—F. L. Evans
Attorney, Agent, or Firm—Bruce A. Walker; William H. Magidson; Ralph C. Medhurst

[57] ABSTRACT

An apparatus and method are disclosed for measuring the fluorescence and absorbance of a liquid sample. A sample tube is provided that has an external surface and a bore therethrough for containing a sample fluid. A cladding fluid coats the bore of the sample tube to provide a smooth surface adjacent to the sample fluid. Excitation radiation is directed along the bore and detector means are provided to detect the excitation radiation, fluorescent radiation, and non-absorbed radiation. Comparator means compare the signals from the presence and concentration of various constituents in the liquid sample.

7 Claims, 3 Drawing Sheets

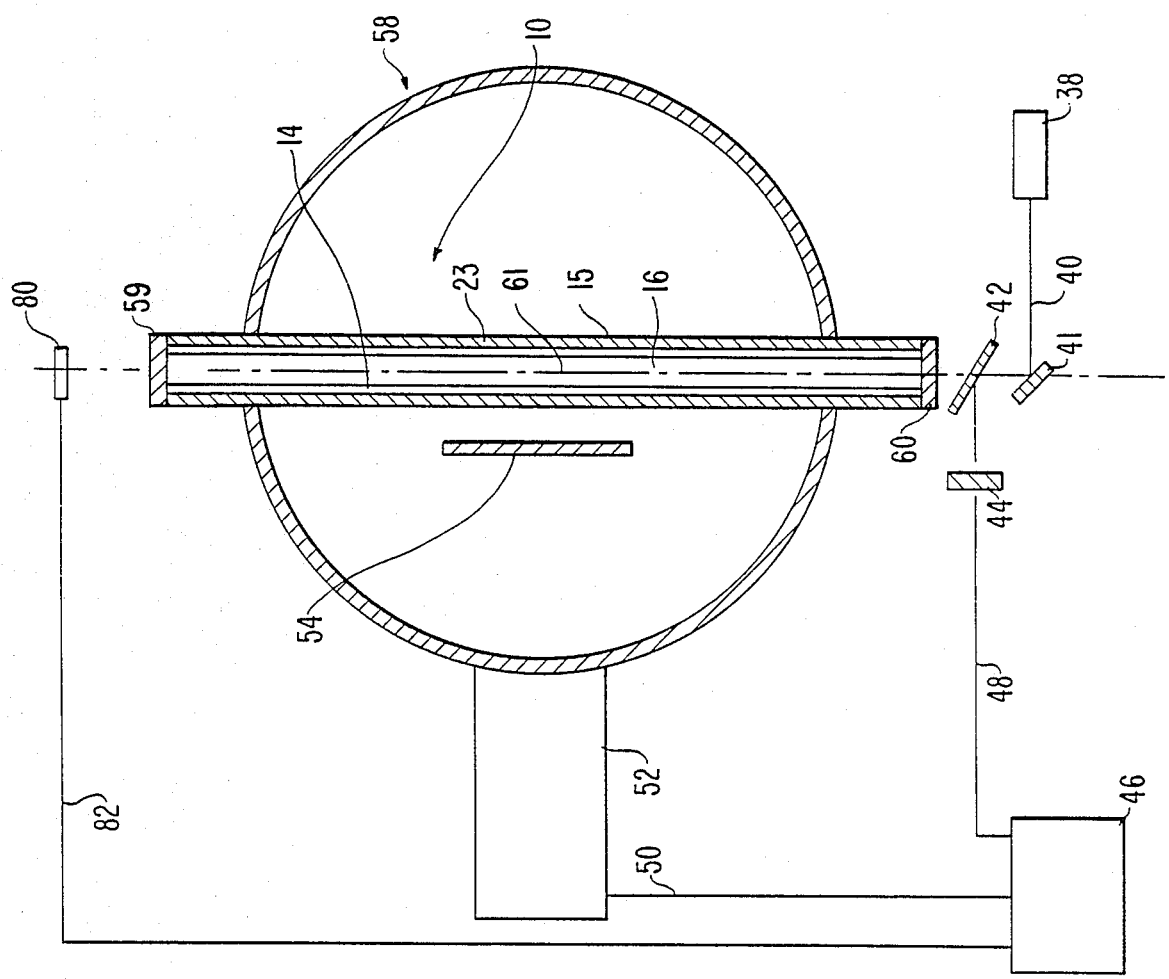

LIQUID/LIQUID FIBER-OPTIC FLUORESCENCE DETECTOR AND ABSORBANCE ANALYZER

BACKGROUND OF THE INVENTION

The present invention relates to fluorescence detectors and, more particularly, to such detectors in which the sample is disposed in a tube, such as a capillary tube.

As discussed in "Fluorescence Analysis of Picoliter Samples," Edmund A. Claude, Mroz and Lechene, Analytical Biochemistry 102, 90–96 (1980), biochemical analysis of very small samples—on the order of picoliters—is required in both basic and applied sciences of cell biology. As explained, many attempts to analyze such samples have been tried, and many of these attempts have used microfluorescence methods. These methods have limitations, however, in the compounds that can be analyzed and the ease with which assays can be performed. The apparatus disclosed in the above-referenced article includes a fluorometer chamber, created optically by using a capillary tube as a flow-through cell, and a microscope-fluorometer to excite fluorescence in and to record fluorescence from the fluorometer chamber within the capillary. Excitation radiation is directed transverse to the capillary tube and fluorescent radiation is similarly collected transverse to the capillary tube.

Such an apparatus has inherent problems in that the excitation radiation is not efficiently delivered to the sample volume since it is directed transverse to the capillary tube and, consequently, passes through only a small portion of the sample volume. Similarly, the fluorescent radiation cannot be efficiently collected and delivered to a detector. The cumulative loss of excitation and fluorescent radiation results in an instrument having greatly reduced sensitivity. Further, such devices cannot accurately or efficiently measure the absorbance characteristics of liquid samples.

It is further desired that fluorescence detectors have provisions for reaction and sample blanking, sample blanking being the signal representing the sample's detection background.

It is also desirous that such a detector be reliable and have low manufacturing costs.

SUMMARY OF THE INVENTION

It is an object of the present invention to provide a fluorescence detector capable of measuring the fluorescence of small sample volumes.

It is a further object of this invention to provide an absorbance detector and analyzer to measure the absorbance of small sample volumes.

It is a still further object of this invention to provide such a fluorescence detector wherein the excitation radiation is efficiently delivered to the sample and the fluorescence radiation from the sample is efficiently collected and detected.

It is a still further object of the present invention to provide a fluorescence detector that has provisions for reactions and sample blanking.

It is a still further object of the present invention to provide a fluorescence detector that is reliable and that has low manufacturing costs.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the apparatus for measuring the fluorescence and absorbance of a liquid sample, wherein the liquid sample is disposed in the bore of a sample tube, comprises: a sample tube for containing a sample fluid having an external surface and a bore therethrough; a cladding fluid for coating the bore of the sample tube to provide a smooth surface adjacent to the sample fluid; a source of excitation radiation directed along the bore of the sample tube; fluorescence detector means for detecting fluorescence radiation emanating from the external surface of the sample tube and generating a fluorescence signal in proportion thereto; and absorbance detector means for detecting the excitation that passes through the bore of the sample tube and generating an absorbance signal in proportion thereto.

The accompanying drawings which are incorporated in and constitute a part of the specification, illustrate one embodiment of the invention and, together with the description, serve to explain the principles of the invention.

BRIEF DESCRIPTION OF THE DRAWINGS

FIG. 5 is a side-sectional view of a second embodiment of a radiation detector and analyzer in accordance with the present invention.

DESCRIPTION OF THE PREFERRED EMBODIMENT

Reference will now be made in detail to the present preferred embodiments of the invention, examples of which are illustrated in the accompanying drawings.

Figure 1:
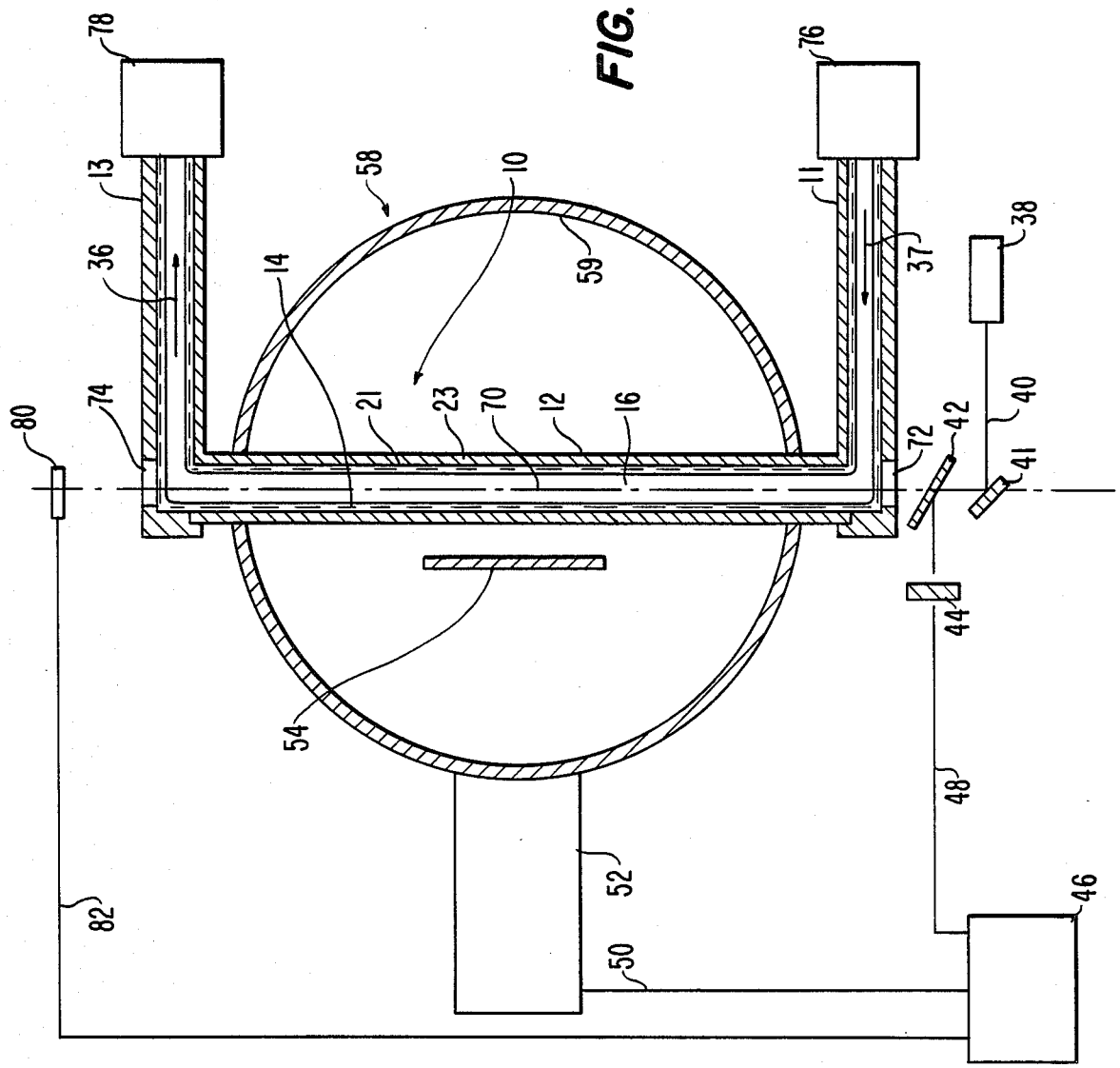
FIG. 1 is a side-sectional view of an embodiment of a radiation detector and analyzer in accordance with the present invention.

One preferred embodiment of an apparatus, in accordance with the present invention, for measuring the fluorescence of a liquid sample, wherein the liquid sample is disposed in the bore of a sample tube, is shown in FIG. 1. This apparatus includes a sample tube for containing a sample fluid having an external surface and a bore therethrough. As embodied herein, the sample tube, represented generally by the numeral 10, is that portion of a flow cell that lies along an axis 70. The flow cell includes a capillary tube 23 having an external surface 12, an internal surface 21, and having a bore 16 of a generally cylindrical shape that extends the length of the capillary tube 23. The axis 70 is the axis of rotation of the bore 16. The term "flow cell" refers to a capillary tube through which a sample to be examined is made to flow. Measurements of a sample in a flow cell can be made either when the sample is in a flowing or stopped flow state.

In accordance with the invention, the apparatus for measuring the fluorescence of a liquid sample includes a cladding fluid for coating the bore of the sample tube to provide a smooth surface adjacent to the sample fluid. As embodied herein the internal surface 21 of capillary tube 23 is coated with a cladding fluid 14. The cladding fluid 14 is a fluorocarbon, that is a viscous, inert, immiscible, nonwetting material that coats the internal surface 21 of the capillary tube 23. Cladding fluids include, for example, fluorocarbon oil. Such flourinated oils are, for example, Krytox available from the DuPont corporation of Wilmington, Del. or Flourinert available from the 3M Corporation of St. Paul, Minn.

In accordance with the invention the apparatus includes a source of excitation radiation directed along the bore of the sample tube. As embodied herein a radiation source 38, such as a laser or a narrow-band filtered multi-wavelength source is provided to supply excitation radiation. Radiation emanating from the radiation source 38 traverses a radiation path 40 defined by a mirror 41 and a beamsplitter 42. Light traversing path 40 passes through an optical window 72 in a first section 11 and into the bore 16 of the capillary tube 23 and travels along axis 70. The window section in the first section 11 is substantially transparent to excitation radiation. The first section 11 places the capillary tube 23 into liquid communication with sample supply means (not shown) via a feed path 37. A second section 13 is provided opposite the capillary tube 23 from the first section 11. The second section 13 joins the capillary tube 23 to the sample supply means (not shown) via a return path 36. A second optical window 74 in the second section 13 is substantially transparent to the excitation radiation. Excitation radiation traversing the bore 16 along axis 15 thus passes through the second window 74 in the second section 13. The cladding fluid 14 is also supplied to the capillary tube 23 via the feed path 37 from cladding fluid supply means 76. The cladding fluid 14 is discarded inot a fluid discard means 78 via path 36.

Thus, in the embodiment of the invention shown in FIG. 1 both the sample fluid and the cladding layer 14 flow through the bore 16 of the capillary tube 23.

The beamsplitter 42 directs a portion of the radiation traversing path 40 towards a reference detector 44. In proportionate response to radiation incident on the detector 44 it generates a signal that is conveyed by a first signal line 48 to a comparator means 46. The purpose and function of the comparator means 46 will be more fully explained hereinbelow.

Figure 2:
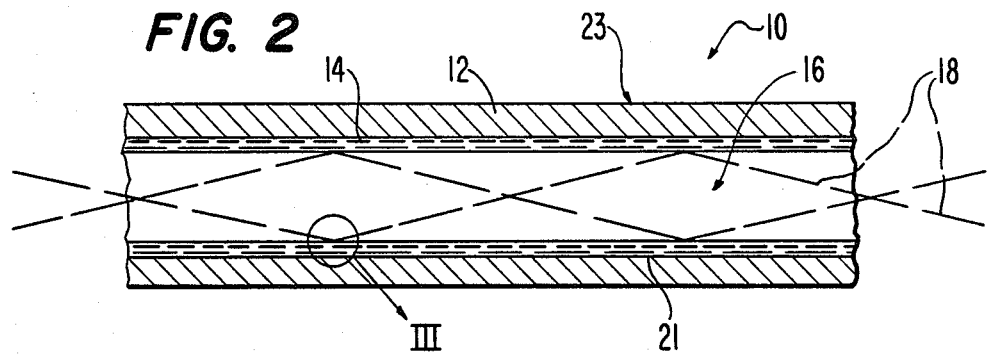
FIG. 2 is a partial cross-sectional view of a capillary tube having a liquid cladding layer in accordance with the present invention.
Figure 3:
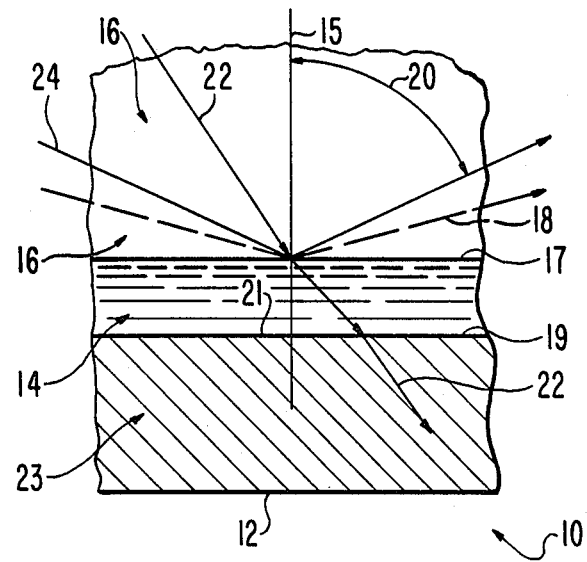
FIG. 3 is an enlarged view of area III of FIG. 2.
Figure 4:
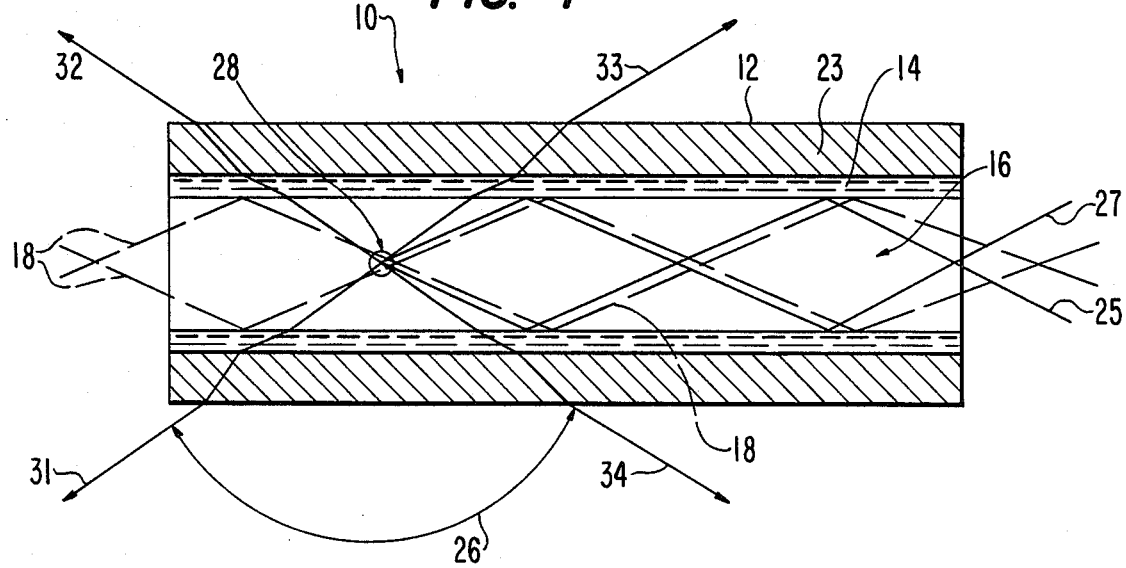
FIG. 4 is a partial sectional view of a capillary tube having a liquid cladding layer and a sample particle in solution excited by exciting radiation in accordance with the present invention.

Turning now to FIGS. 2, 3 and 4 the structure and function of the sample tube 10 is illustrated.

FIG. 2 is a partial cross-sectional view of a sample tube 10 having a liquid cladding layer 14 in accordance with the present invention. For the purpose of illustration the size and proportions of the various component parts of the sample tube 10 of FIG. 2 are shown exaggerated. Radiation rays 18 of excitation radiation propagate along the bores 16 of the capillary tube 23. The radiation rays 18 are internally reflected by the surface of the cladding layer 14.

It is a well known principle of optics that at the interface between a first medium of a first index of refraction and a second medium having a second, lower, index of refraction there exist a range of incident angles at the interface for which no refracted radiation is possible. In the limiting case, where the rays passing through the first medium are incident on the second medium, the incident rays approach a fixed angle, $\theta c$, beyond which no refracted light is possible. This fixed angle is called the critical angle and can be calculated as follows:

$$\mathrm{Sin}\theta c = n_z/n_1$$

where:
$\theta c$ = critical angle
$n_1$ = index of refraction of the first medium
$n_z$ = index of refraction of the second medium The present invention takes advantage of this principle to ensure that the excitation radiation rays 18 propagate along the length of the bore 16. Thus, it can be assured that the fluorescent samples entrained in the sample fluid passing through or stopped in the bore 16 will be efficiently excited by the excitation radiation rays 18.

FIG. 3 is an enlarged view of the area deliniated by the circle III in FIG. 2.

It can be appreciated that with the internal surface 21 of the capillary tube 23 coated with a cladding fluid 14 and a fluorescent sample contained in the bore 16 two boundaries are defined by the system. A first boundry 17 is the interface between the fluorescent sample and the cladding fluid 14. A second boundry 19 is defined by the interface between the cladding fluid 14 and the capillary tube 23 at the internal surface 21 of the capillary tube 23.

The cladding fluid 14, creates an internal cladding layer on the bore 16 of the capillary tube 23. The fluorescent sample is contained within the cladding layer 14. Excitation radiation passing through the bore of the capillary tube 23 will be internally reflected at the boundry 17 if the angle of incidence that such rays of radiation make with the interface 17 is below the critical angle. The critical angle 20 is high and the excitation rays will be matched to this angle. The high critical angle 20 will assist the emission efficiency of the fluorescent sample in question.

A line 15, shown in FIG. 3, is normal to the surface of the cladding layer 14 and to the surface of the capillary tube 23. The critical angle 20 is defined as that angle, above which internal reflections of rays, such as ray 18 and ray 24 occur. Rays, such as ray 22, which are incident on the cladding layer 14 at an angle less that the critical angle 20 will not be internally reflected at the interface 17 but will rather pass into the cladding fluid 14 through the internal wall 21 of the capillary tube 23 and pass through the surface 12 of the capillary tube 23.

The low angle multiple reflections of the excitation radiation at the interface 17 ensures that the excitation radiation is retained within the bore 16 of the capillary tube 23 so as to excite the fluorescent sample in a manner described hereinbelow in reference to FIG. 4. Thus, exposure of the sample to excitation occurs along the axis of the bore 16 that encapsulates the sample. This long path length exposure also enhances fluorescence excitation.

As an example, consider a fluorescent sample having an index of refraction of approximately 1.33 along with the cladding fluid having an index of refraction of approximately 1.29. The cladding fluid with its lower index of refraction, will create an internal cladding layer on the inner wall 21 of the capillary tube 23. The critical angle can be calculated as follows:

$$n \sin(z) = n' \sin(z')$$

where:
n = the index of refraction of the fluorescent sample = 1.3 n = the index of refraction of the cladding fluid = 1.29, and
z' = 90°
sin(z) = 1.29/1.33
z = 75.9°

Thus, the critical angle for the sample/cladding interface = 75.9°.

The critical angle for a glass/air interface at surface 12 can be calculated, for example, as follows:

$$n \sin(z) = n' \sin(z')$$

where:
n = the index of refraction of glass = 1.46
n' = the index of refraction of air = 1.00
z' = 90°
sin(z) = 1.00/1.46
z = 43.2°

Thus, the critical angle for a glass/air interface at surface 12 is 43.2°.

FIG. 4 illustrates the excitation of a fluorescent sample volume 28 by excitation radiation 18. The fluorescent volume 28, upon being struck by excitation radiation 18, fluoresces. The fluorescent radiation takes numerous paths, several of which are depicted by beams 31-34 and 25 and 27. If the flourescent radiation angle of incidence with the cladding layer 14 is larger than the critical angle it will be internally reflected, as shown by rays 25 and 27. If the angle of incidence of the fluorescent radiation is less than the critical angle, as defined in reference to FIG. 3, it will pass through the cladding layer 14 and the capillary tube 23 as depicted by rays of fluorescent radiation 31-34. Thus, all fluorescent radiation emanating from the fluorescent sample volume and within the included angle 26 will emanate from the external surface 12 of the capillary tube 23.

In accordance with the present invention the apparatus includes fluorescence detector means for detecting fluorescence radiation emanating from the external surface of the sample tube and generating a fluorescence signal in proportion thereto. As embodied herein, and illustrated in FIG. 1, this fluorescence detector means includes a photomultiplier tube 52. The photomultiplier tube 52 generates a signal in proportion to the radiation incident on it which is passed by a signal line 50 to the comparator 46.

An integration sphere 58 is provided to capture and integrate the fluorescence energy from the sample tube 10. Thus, radiation that emanates from the sample tube 10 through its outer surface 12 is captured by the integrating sphere 58 and integrated. The integration sphere 58 includes an internal surface 59 that diffusely reflects the radiation emanating from the sample tube 10 a plurality of times in a random fashion until the radiation is absorbed by the internal surface 59, passes back into the sample tube 10 or falls incident on the photomultiplier tube 52.

A source baffle 54 is provided to ensure that no direct sample excitation radiation falls incident on the photomultiplier tube 52, since only reflected radiation is accepted by the photomultiplier tube 52.

For a more complete description of the construction and manner of operation of integrating spheres attention is invited to a publication entitled "Integrating Sphere Performance," copyrighted in 1981, by D. J. Lovell of Labsphere North Sutton, N.H. 03260, which is incorporated herein by reference.

In accordance with the present invention the apparatus includes absorbance detector means for detecting radiation that passes through the bore of the sample tube and generating an absorbance signal in proportion thereto. It is known in the art of chemical analysis that various samples absorb radiation of specific wavelengths in a predictable fashion. By measuring the amount of excitation radiation absorbed by the sample, therefore, and comparing it with the reference signal from detector 44 in the comparator means 46 the presence and concentration of various constituents in the sample in the sample tube 10 can be determined. As embodied herein, the absorbance detector 80 is provided adjacent the second window 74 to collect the radiation emanating from the sample tube 10. The signal generated by the absorbance detector 80 is passed along a line 82 to the comparator means 46.

The comparator 46 compares the signals from the reference detector 44, the absorbance detector 80 and the photomultiplier 52. Briefly, and as is known to those skilled in the art, the comparator means 46 receives a signal along line 48 from the reference detector 44 that is indicative of the intensity of the excitation radiation emanating from the excitation radiation source 38. In addition, the comparator means 46 receives a signal from the photomultiplier 52 along line 50 that is proportional to the fluorescence radiation emanating from the sample contained in the bore 16 of the capillary tube 10. Both the reference detector 44 and the photomultiplier 52 are responsive to the wavelength of excitation and fluorescence radiation, respectively incident thereon. Thus, by comparing the relative outputs from the reference detector 44 and the photomultiplier 52 the presence and concentration of fluorescence particles 28 in the sample fluid can be ascertained. In addition, the signal from the absorbance detector 80 is processed in the manner described above to yield more information about the constituent parts of the sample contained in the sample tube 10.

FIG. 5 shows a second embodiment of the present invention wherein the cladding fluid 14 and the fluorescent sample are both static within the sample tube 10. In this embodiment the sample tube 10 comprises a discrete capillary tube that can be sealed at one or both ends by end caps 58 and 60. The end caps 58 and 60 are transparent to excitation radiation emanating from the excitation radiation source 38. The exciting radiation traversing path 40 thus passes through the end cap 60 and into the bore 16. That portion of the excitation radiation that traverses the bore 16 passes through the end cap 58 along a path 56, to fall incident on the absorbance detector 80.

The manner of propagation of the excitation radiation in the bore 16 of the sample 10 of FIG. 5 is the same as described in reference to FIGS. 2, 3 and 4. Similarly samples are excited and the fluorescent radiation detected and the signal processed in the manner described in reference to FIG. 1. Further, the absorbance in the manner previously described.

It will be apparent to those skilled in the art to which the present invention pertains that various modifications and variations can be made in the fluorescence detector of the present invention and in the construction of the sample tube 10 without departing from the scope or spirit of the invention. Thus, it is intended that the present invention cover the modifications and variations of this invention provided they come within the scope of the appended claims and their equivalents.

What is claimed is:

1. An apparatus for measuring the fluorescence and absorbance of a liquid sample, wherein the liquid sample is disposed in the bore of a sample tube, comprising:
   a sample tube for containing a sample fluid having an external surface and a bore therethrough;
   a source of excitation radiation directed along said bore of said sample tube;
   cladding fluid means coating said bore of said sample tube effective to reflect said excitation radiation radially inwardly within said bore and further effective to provide a smooth surface adjacent to the sample fluid;
   fluorescence detector means for detecting fluorescence radiation emanating from said external surface of said sample tube and generating a fluorescence signal in proportion thereto; and
   absorbance detector means for detecting the excitation radiation that passes through the bore of the sample tube and generating an absorbance signal in proportion thereto.

2. An apparatus as claimed in claim 1, wherein said cladding fluid has an index of refraction less than that of said sample fluid.

3. An apparatus as claimed in claim 1, that further includes:
   a reference detector for detecting the intensity of said source radiation and for generating a reference signal in proportion thereto;
   comparator means for comparing the reference signal, the fluorescence signal and the absorbance signal to determine the chemical characteristics of the sample fluid.

4. An apparatus as claimed in claim 3, wherein said sample tube in a flow cell.

5. An apparatus as claimed in claim 3, wherein said sample tube is a discrete capillary tube.

6. An apparatus as claimed in claims 4 or 5 that further includes:
   an integrating sphere surrounding said sample tube to capture and integrate fluorescence radiation emanating from said external surface of said sample tube; and
   said fluorescence detector means being a photomultiplier tube in radiation communication with said integration sphere.

7. A method of measuring the fluorescence of a liquid sample, wherein the liquid sample is disposed in the bore of a capillary tube, comprising:
   cladding the bore of the capillary tube with a cladding fluid;
   disposing the liquid sample in the bore of the capillary tube radially inwardly from the cladding fluid;
   directing a source of excitation radiation along the bore of the capillary tube through the liquid sample;
   detecting the intensity of the excitation radiation, the intensity of fluorescent radiation emanating from the liquid sample, and the intensity of the non-absorbed excitation radiation passing through the sample;
   comparing the intensities of the detected excitation radiation, the fluorescent radiation, and the non-absorbed excitation radiation to determine the presence and concentration of fluorescent particles in the liquid sample;
wherein said cladding fluid is effective to reflect said excitation radiation radially inwardly within said bore and is further effective to provide a smooth surface adjacent to the liquid sample.

* * * * *

UNITED STATES PATENT OFFICE
CERTIFICATE OF CORRECTION

Patent No. 4,867,559          Dated September 19, 1989

Inventor(s) David T. Bach

It is certified that error appears in the above-identified patent and that said Letters Patent is hereby corrected as shown below:

| Column | Line | |
|---|---|---|
| 3 | 55 | "bores" should read --bore-- |
| 4 | 41 | "that" should read --than-- |
| 4 | 68 | "1.3" should read --1.33-- |
| 5 | 1 | "n" should read --n'-- |
| 6 | 57 | "absorbance in" should read --absorbance characteristics of the sample are detected and processed in-- |
| 7 | 36 | "in" should read --is-- |

Signed and Sealed this

Ninth Day of October, 1990

Attest:

HARRY F. MANBECK, JR.

Attesting Officer    Commissioner of Patents and Trademarks